United States Patent [19]

Harbeke et al.

[11] Patent Number: 4,766,317
[45] Date of Patent: Aug. 23, 1988

[54] OPTICAL REFLECTANCE METHOD OF EXAMINING A SIMOX ARTICLE

[75] Inventors: Guenther Harbeke, Affoltern am Albis, Switzerland; Lubomir L. Jastrzebski, Plainsboro, N.J.

[73] Assignee: General Electric Company, Schenectady, N.Y.

[21] Appl. No.: 41,565

[22] Filed: Apr. 23, 1987

[51] Int. Cl.$^4$ .................. G01N 23/00; G01T 1/22; G01J 1/42

[52] U.S. Cl. .................. 250/358.1; 250/370.01; 250/372

[58] Field of Search .............. 250/358.1, 359.1, 360.1, 250/370, 371, 372; 356/51, 237

[56] References Cited

U.S. PATENT DOCUMENTS 4,352,016  9/1982  Duffy et al. .................. 250/358.1
4,352,017  9/1982  Duffy et al. .................. 250/358.1
4,511,800  4/1985  Harbeke .................. 250/372

Primary Examiner—Eugene R. Laroche
Assistant Examiner—David Mis
Attorney, Agent, or Firm—Henry I. Steckler; James C. Davis, Jr.; Paul R. Webb, II

[57] ABSTRACT

The present invention provides an optical method of quickly, easily, and accurately determining the degree of amorphism, surface roughness, and presence of a contaminating film on the surface of a SIMOX article. The reflectances of the SIMOX material and a reference single crystalline silicon material are compared. Reflectances are obtained at three selected wavelengths and used to evaluate three simultaneous equations which yield values for the parameters A, B, and C when A, B, and C represent the degree of amorphism, surface roughness, and surface contamination respectively.

5 Claims, 2 Drawing Sheets

OPTICAL REFLECTANCE METHOD OF EXAMINING A SIMOX ARTICLE

This invention was made with Government support under contract number F19628-86-C-0086 awarded by the Department of the Air Force. The Government has certain rights in this invention.

The present invention relates to the examination of a SIMOX article to determine its degree of amorphism, surface roughness, and surface contamination.

BACKGROUND OF THE INVENTION

Among various Silicon on Insulation (SOI) approaches SIMOX (separation by oxygen implantation) seems to be the most promising as a replacement for use of silicon on sapphire (SOS) in CMOS processing. During the SIMOX process oxygen at the dose of about $1.0-2.0 \times 10^{18}$ atoms cm$^{-2}$ is implanted into a silicon wafer with energy of about 150–200 keV, at the temperature range of about 450°–650° C. To remove the implantation damage and to form a buried oxide, the SIMOX wafers are subsequently annealed at a temperature in the range from 1150° to 1400° C. A typical SIMOX structure is shown in FIG. 1 wherein a wafer 10 includes an oxygen implanted layer 12 and a regrown SIMOX film 14. A thin surface layer ($\approx$10–20 nm) of the SIMOX wafers serves as a seed during the solid state regrowth process. The degree of crystalline perfection of this layer will influence the crystallographic perfection of the regrown SIMOX film 14.

In order to predict the properties of SIMOX material after annealing that affect device performance, it is important to know the properties of the seed layer (degree of amorphism) after implantation. A second important parameter which will influence device performance is the roughness of the silicon surface. Faster erosion of silicon in the places exposed to hot spots in an ion beam could give a nonuniform, rough surface. A third important parameter which should be monitored is the presence of contaminations (e.g., carbon) which can form a thin film on SIMOX surfaces.

It would obviously be desirable to be able to examine a given SIMOX wafer and easily determine these three parameters, that is, amorphism, surface roughness, and surface contamination, prior to investment of substantial effort in the fabrication of integrated circuit devices. Methods have been developed which can be used to determine the crystalline quality of a semiconductor surface. Such a method is described in U.S. Pat. No. 4,352,016, which issued Sept. 28, 1982 to Duffy et al. Duffy et al. utilizes the reflections from two different wavelengths of light one of which is sensitive to both the physical and crystalline perfection of the surface being examined and the other of which is only sensitive to the physical perfection. By knowing the interrelationship between these two parameters and the reflectance characteristics of the surface for the particular wavelengths of light being used, the crystalline quality of the surface can be determined. Another method which utilizes reflectance of two different wavelengths of light is disclosed in U.S. Pat. No. 4,511,800 which issued Apr. 16, 1985 to Harbeke et al. Harbeke et al. chose the wavelengths of light so that the reflectance of one is sensitive to surface roughness while the other is sensitive to both the surface roughness and amorphism of the film being examined. Again, by knowing the interrelationship between these two parameters and the reflectance characteristics of the surface for the particular wavelengths of light being used, one or the other of the parameters can be determined.

SUMMARY OF THE INVENTION

The present invention includes a method for determining the degree of amorphism, surface roughness, and surface contamination of a SIMOX article. The ultraviolet reflectances $R_{367}$, $R_{320}$, and $R_{240}$ of the SIMOX article are determined when illuminated with light having wavelengths of about 367 nm, 320 nm, and 240 nm respectively. Unique values for A, B, and C are determined by means of:

$$\Delta R_{367} = A + C + B(1/0.367)^4$$

$$\Delta R_{320} = C + B(1/0.320)^4$$

$$\Delta R_{240} = C + B(1/0.240)^4$$

wherein A, B, and C represent the degree of amorphism, surface roughness, and surface contamination respectively.

DESCRIPTION OF THE PREFERRED EMBODIMENT

The present invention is based upon the discovery that light of certain selected frequencies can be used to determine the degree of amorphism, surface roughness, and surface contamination of SIMOX articles such as SIMOX films on semiconductor wafers. It has been discovered that by illuminating the SIMOX surface with light beams of three different wavelengths, 240 nm, 320 nm, and 367 nm, the reflections of these light beams will indicate various changes of reflectance corresponding to amorphism, surface roughness, and the presence of a surface contaminating film. These changes of reflectance, which are indicated by the measured reflectance at each of these wavelengths, are embodied in the following equations:

$$\Delta R_{367} = A + C + B(1/0.367)^4 \qquad (1)$$

$$\Delta R_{320} = C + B(1/0.320)^4 \qquad (2)$$

$$\Delta R_{240} = C + B(1/0.240)^4 \qquad (3)$$

where $\Delta R_{367}$, $\Delta R_{320}$, and $\Delta R_{240}$ are the differences between the measured reflectances of the SIMOX surface and the reference single crystalline surface at wavelengths of 367 nm, 320 nm, and 240 nm respectively. A represents the degree of amorphism of the SIMOX film, B represents the surface roughness, and C represents the effect of the presence of a foreign film on the SIMOX surface.

The above equations (1), (2), and (3) assume that the spectral dependence of reflection for a foreign film is weak. That is, that the effect that the film has on the reflection will be substantially independent of the wavelength of the light. This assumption is valid where the surface contamination is silicon carbide or semi-insulating polycrystalline oxygen-doped silicon (SIPOS). These are the contaminates which are of most concern when examining SIMOX wafers for quality.

The actual apparatus for illuminating the SIMOX article and determining the value of the reflection is not important to the teachings of the present invention. Any suitable reflectometer may be used such as the reflectometer described in U.S. Pat. No. 4,352,017, which issued Sept. 28, 1982 to Duffy et al. Standard techniques for operating the reflectometer are set forth in U.S. Pat. No. 4,352,016, which issued Sept. 28, 1982 to Duffy et al. and U.S. Pat. No. 4,511,800, which issued Apr. 16, 1985 to Harbeke et al. These well known techniques are suitable for use in practicing the teachings of the present invention.

Figure 1:
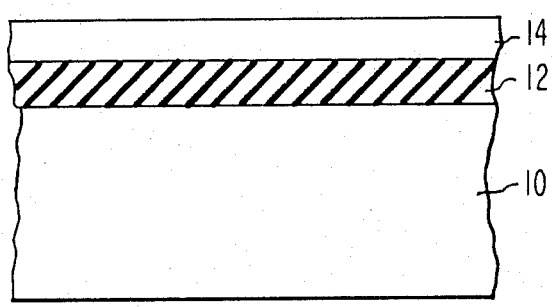
FIG. 1 is a partial cross-sectional view of a SIMOX wafer.
Figure 2:
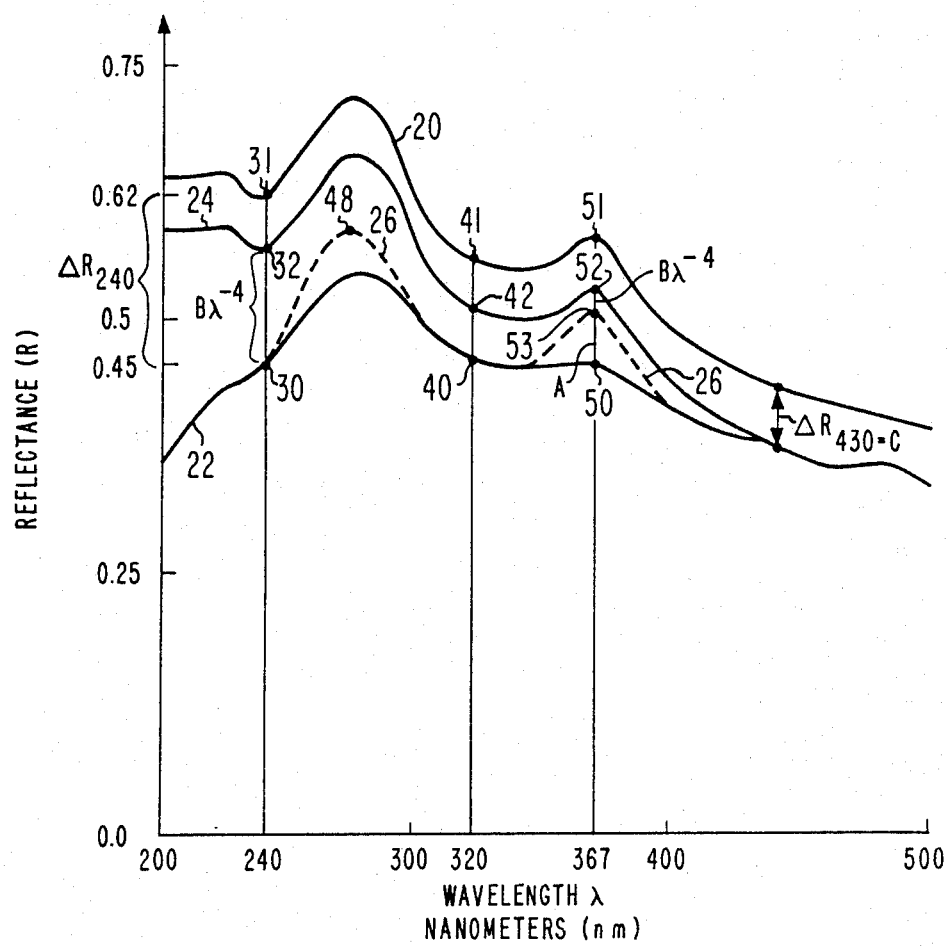
FIG. 2 is a graph showing the ultraviolet reflectance spectrum for single crystalline silicon and SIMOX film.

The following discussion will provide an intuitive understanding of the derivation of equations (1), (2), and (3). FIG. 2 shows a reflectance spectrogram or plot 20 for a reference single crystalline silicon surface and a reflectance spectrogram or plot 22 for a typical SIMOX wafer surface. Both spectrograms have a range of from 200 nm to 500 nm, however, the meaningful information with respect to the present invention is for wavelengths less than 400 nm. The points of interest of these two plots 20 and 22 for the wavelengths of 240 nm, 320 nm, and 367 nm are indicated as 30, 31, 40, 41, 50, and 51 respectively. The reflectance value R of these points may be read on the ordinate scale which indicates percent of total reflectance. Therefore, the value of $\Delta R$ of a particular wavelength is equal to the value of the reflectance of single crystalline silicon minus the value of the reflectance of the SIMOX film at that wavelength. For example, $\Delta R_{240}$ is equal to the value of the reflectance at the point 31 less the value of the reflectance at the point 30, $0.62 - 0.45 = 0.17$. Similarly, $\Delta R_{320}$ and $\Delta R_{367}$ are equal to the difference in values of reflectance at the points 41 and 40 and the points 51 and 50 respectively.

A first corrected plot 24 which represents the spectrogram 20 for single crystalline silicon corrected for the presence of a surface contaminating film is shown between the plots 20 and 22. Note that the plot 24 intersects the 240 nm, 320 nm, and 367 nm wavelengths at the points 32, 42, and 52 respectively. It will be further noted that at a wavelength of about 430 nm the plot 24 merges with the plot 22 indicating that at that wavelength the contaminating film accounts for the entire reflectance difference $\Delta R_{430}$ which will hereinafter be referred to as C. Therefore, the ordinate values for the plot 20 for single crystalline silicon is simply reduced by an amount equal to C to obtain the first corrected plot 24. Now, since a specific identifiable portion of $\Delta R$, the portion between the point 51 and 52 of $\Delta R_{367}$ for example, is solely attributable to a contaminating film while the remainder of $\Delta R$, that is the portion between the points 50 and 52, is attributable to other causes. These other causes are, as is well known in the art, the degree of amorphism and surface roughness of the SIMOX film.

Figure 3:
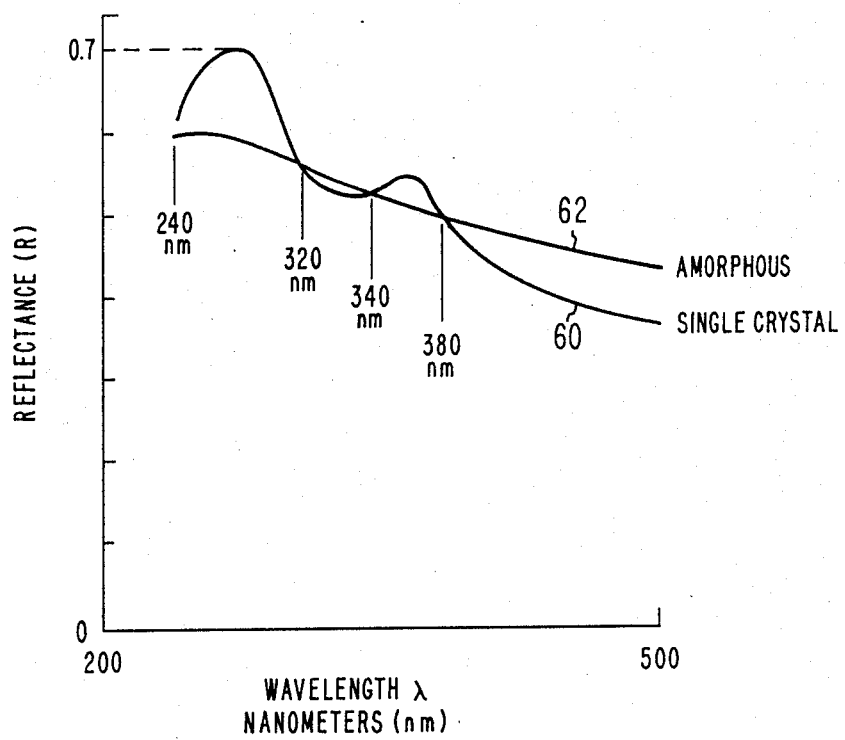
FIG. 3 is a graph showing the ultraviolet reflectance spectrum for single crystalline silicon and amorphous silicon.

It has been discovered that the value of the reflectance (R) at wavelengths of about 240 nm and 320 nm is not affected by the degree of amorphism of the SIMOX film, but is only affected by the degree of surface roughness and the presence of a contaminating film. This is illustrated in FIG. 3 where there is shown a reflectance spectrogram or plot 60 for single crystalline silicon and a spectrogram or plot 62 for amorphous silicon. Both spectrograms have a range of from 200 nm to 500 nm. It is seen that the plot 60 intersects the plot 62 at four points coinciding with the wavelength 240 nm, 320 nm, 340 nm, and 380 nm. These wavelengths then, or approximately these wavelengths, result in reflections substantially void of the effects of amorphism. Therefore, $\Delta R$ at any of these four wavelengths will represent the degree of surface roughness and presence of a contaminating film but will not be affected by the degree of amorphism. While all four of these wavelengths may be utilized in the practice of the present invention, data at only two of these wavlengths is needed. For illustrative purposes wavelengths of 240 nm and 320 nm were chosen.

The value of $\Delta R_{240}$ less the value of C, therefore, represents the degree of surface roughness at a wavelength of about 240 nm. Similarly, the value of $\Delta R_{320}$ less the value of C represents the degree of surface roughness at a wavelength of about 320 nm. Surface roughness causes scattering of reflected light (Rayleigh scattering) wherein the amount of scattered light is related to the wavelength of the light. Rayleigh has shown that this value is inversely proportional to the fourth power of the wavelength. That is, the difference between the reflectances R at the points 30 and 32 is equal to $B\lambda^{-4}$ where $\lambda = 240$ nm. Similarly, the difference between the reflectance R at the points 40 and 42 is equal to $B\lambda^{-4}$ when $\lambda = 320$ nm. Therefore, in general, surface roughness is equated to $B\lambda^{-4}$ over the spectrum of 200 nm to 400 nm. The ordinate values of the first corrected plot 24 may now be reduced by an amount equal to $B\lambda^{-4}$ to obtain a second corrected plot 26, which is indicated by dashed lines in FIG. 2.

The second corrected plot 26 is indicative of the degree of amorphism only, that is, the effects of any contaminating film and surface roughness are removed. It will be noted that the second corrected plot 26, peaks at wavelengths of about 270 nm and about 367 nm, at the points 48 and 53 respectively, thereby providing a maximum indication of the degree of amorphism at those wavelengths. While the present invention teaches determining the degree of amorphism at both of the wavelengths, 270 nm and 367 nm, in practice data at only one of these wavelengths is needed. A wavelength of 367 nm was chosen for illustrative purposed herein.

The portion of $\Delta R$ that is solely attributable to amorphism, that is $\Delta R_{367} - C - B\lambda^{-4}$, is equal to A at $\lambda = 367$ nm, as shown in FIG. 2. It will be appreciated that $\Delta R_{367} - C - B\lambda^{-4} = A$ is equivalent to equation (1) above. Further, since C represents the effect of a contaminating film and $B\lambda^{-4}$ represents the degree of surface roughness at both 240 nm and 320 nm, it follows that $\Delta R = C + B\lambda^{-4}$ for those two wavelengths, which are equivalent to equations (2) and (3) respectively.

The important advantage of the present invention is that a rapid characterization technique is provided for easily and accurately determining the degree of amorphism, surface roughness and presence of a contaminating film on the surface of a SIMOX semiconductor wafer. This determination can be made after oxygen implant and prior to substantial investment of effort in the fabrication of integrated circuit devices.

What is claimed is:

1. A method of determining the degree of amorphism, surface roughness and surface contamination of a SIMOX article comprising the steps:

(a) determining the difference in reflectance, $\Delta R_\lambda$, between single crystalline silicon and said SIMOX article at three selected wavelengths of light of $\lambda 1$, $\lambda 2$, and $\lambda 3$;

(b) determining a unique value for A, B, and C by means of:

$$\Delta R_{\lambda 1} = A + C + B(1/\lambda 1)^4$$

$$\Delta R_{\lambda 2} = C + B(1/\lambda 2)^4$$

$$\Delta R_{\lambda 3} = C + B(1/\lambda 3)^4$$

wherein A, B, and C are representative of said degree of amorphism, surface roughness, and surface contamination respectively.

2. The method of claim 1 wherein step (a) inclues the steps:

(a1) illuminating said SIMOX article with light of one of said three selected wavelengths and measuring the level of reflectance $R_\lambda$ for said wavelength of light;

(a2) determining said difference in reflectance $\Delta R_\lambda$ by subtracting said measured level of reflectance $R_\lambda$ from a predetermined level of reflectance of single crystalline silicon for said wavelength of light.

3. The method of claim 2 wherein said wavelength $\lambda 1$ is either about 270 nm or about 367 nm.

4. The method of claim 3 wherein said wavelengths $\lambda 2$ and $\lambda 3$ are different and taken from the group of wavelengths comprising:
about 240 nm;
about 320 nm;
about 340 nm; and
about 380 nm.

5. The method of claim 4 wherein said wavelengths $\lambda 1$ equals about 367 nm, $\lambda 2$ equals about 320 nm, and $\lambda 3$ equals about 240 nm.

* * * * *